United States Patent [19]

Mutoh et al.

[11] Patent Number: 5,004,662
[45] Date of Patent: Apr. 2, 1991

[54] ELECTROPHOTOGRAPHIC PHOTOSENSITIVE MATERIAL CONTAINING M-PHENYLENEDIAMINE COMPOUND

[75] Inventors: Nariaki Mutoh, Daito; Yasuyuki Hanatani, Sakai; Toshihiko Nishiguchi, Moriguchi, all of Japan

[73] Assignee: Mita Industrial Co., Ltd., Osaka, Japan

[21] Appl. No.: 385,433

[22] Filed: Jul. 27, 1989

[30] Foreign Application Priority Data

Jul. 27, 1988 [JP] Japan .................. 63-187312

[51] Int. Cl.$^5$ .................................. G03G 5/09
[52] U.S. Cl. .................................. 430/59; 430/72
[58] Field of Search .................. 430/59, 72, 83

[56] References Cited

U.S. PATENT DOCUMENTS

| | | | |
|---|---|---|---|
| 4,588,666 | 5/1986 | Stolka et al. | 430/96 |
| 4,725,518 | 2/1988 | Carmichael et al. | 430/96 |
| 4,877,702 | 10/1989 | Miyamoto et al. | 430/59 |

Primary Examiner—John Goodrow
Attorney, Agent, or Firm—Sherman and Shalloway

[57] ABSTRACT

Disclosed is an electrophotographic photosensitive material containing in a photosensitive layer an m-phenylenediamine compound represented by the following general formula [I]:

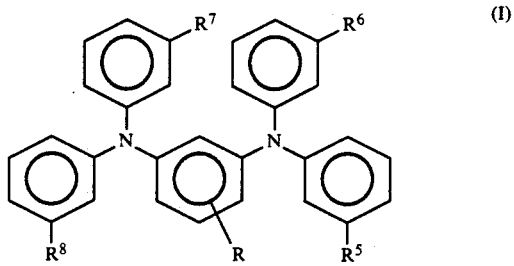

wherein $R^5$, $R^6$, $R^7$ and $R^8$ are groups substituted at meta-positions to the nitrogen atoms and represent a hydrogen atom, an alkyl group, an alkoxyl group or a halogen atom, with the proviso that at least two of $R^5$, $R^6$, $R^7$ and $R^8$ represent an alkyl group, alkoxyl group or a halogen atom, and R represents a hydrogen atom, an alkyl group, an alkoxyl group or a halogen atom.

This meta-substituted m-phenylenediamine compound of general formula [I] is hardly crystallized in a resin but is sufficiently dissolved in the resin, and therefore, the concentration of the compound in the resin can be increased and the mobility can be enhanced. Accordingly, an electrophotographic photosensitive material having an increased sensitivity can be provided.

7 Claims, No Drawings

ELECTROPHOTOGRAPHIC PHOTOSENSITIVE MATERIAL CONTAINING M-PHENYLENEDIAMINE COMPOUND

BACKGROUND OF THE INVENTION (1) Field of the Invention

The present invention relates to an electrophotographic photosensitive material comprising an m-phenylenediamine compound as a charge transport substance.

(2) Description of the Related Art

An organic photosensitive material which has a good processability, is advantageous from the viewpoint of the manufacturing cost and has a large freedom of design of functions is recently used as an electrophotographic photosensitive material in an imageforming apparatus such as a copying machine. Especially, photosensitive layers comprising a charge generating material capable of generating charges under irradiation with light and a charge transport material for transporting the generated charges, for example, function-separated single-layer type photosensitive materials comprising a charge generating material, a charge transport material and a binder resin, and function-separated electrophotographic photosensitive materials having a laminate type photosensitive layer having a laminate structure comprising a charge generating layer containing a charge generating material as described above and a charge transport layer containing a charge transport material as mentioned above, have been proposed.

The Carlson process is widely used for forming a copied image by using an electrophotographic photosensitive material. The Carlson process comprises, in principle, the charging step of uniformly charging a photosensitive material by corona discharge, the light-exposure step of exposing the charged photosensitive material imagewise to light to form an electrostatic latent image corresponding to an original image, the developing step of developing the electrostatic latent image with a developer containing a toner to form a toner image, the transfer step of transferring the toner image to a substrate such as a paper sheet, the fixing step of fixing the toner image transferred onto the substrate, and the cleaning step of removing the toner left on the photosensitive material after the transfer step. In order to form a high-quality image in this Carlson process, it is required that the electrophotographic photosensitive material should be excellent in charging characteristics and photosensitive characteristics, and the residual potential after the light exposure should be low.

In the above-mentioned function-separated electrophotographic photosensitive material, the electric characteristics and photosensitive characteristics of the photosensitive material are greatly influenced by the characteristics of the charge generating material and charge transport material. Accordingly, various substances have been examined, and polyvinyl carbazoles, oxadiazole compounds, pyrazoline compounds and hydrazone compounds have been proposed as the charge transport material.

However, in these charge transport materials, the drift mobility indicating the charge transport capacity is relatively small. Moreover, the dependency of the drift mobility on the electric field intensity is large, and therefore, the migration of charges in a low electric field is small and cancellation of the residual potential is difficult. Moreover, these charge transport materials are readily deteriorated under irradiation with ultraviolet rays and the like.

It is known that the electric field dependency of the drift mobility is small in the triphenylamine type charge transport material. For example, U.S. Pat. No. 3,265,496 proposes N,N,N',N'-tetraphenylbenzidine, N,N,N',N'-tetraphenyl-1,4-phenylenediamine and N,N,N',N'-tetraphenyl-1,3-phenylenediamine. However, these charge transport materials are still defective in that the sensitizing effect is low in the ordinary application and if the amount added is increased, crystallization is often caused. Therefore, these charge transport materials cannot be put into practical use.

For overcoming this defect, we previously proposed m-phenylenediamine compounds, in which phenyl groups of N,N,N',N'-tetraphenyl-1,3-phenylenediamine can optionally be substituted, so far as the substitution is possible (see Japanese Patent Application No. 62-301703).

Certain improvements can be attained by introduction of substituents, but it has been found that the improvements are still insufficient.

In general, the characteristics of an electrophotographic photosensitive material are greatly influenced by the photoconductive material used, though the influences differ more or less according to the object and preparation process.

SUMMARY OF THE INVENTION

Under this background, we made research and as the result, it was found that if, of the foregoing m-phenylene-diamine compounds, a compound in which respective substituents are located at meta-positions to nitrogen atoms with respect to phenylene groups is selected and used for the preparation of an electrophotographic photosensitive material, this compound is hardly crystallized in a binder resin.

It is therefore a primary object of the present invention to provide a photoconductive substance which is hardly crystallized in a resin and also provide a high-sensitivity electrophotographic photosensitive material comprising this photoconductive substance.

More specifically, in accordance with the present invention, there is provided an electrophotographic photosensitive material containing in a photosensitive layer an m-phenylenediamine compound represented by the following general formula [I]:

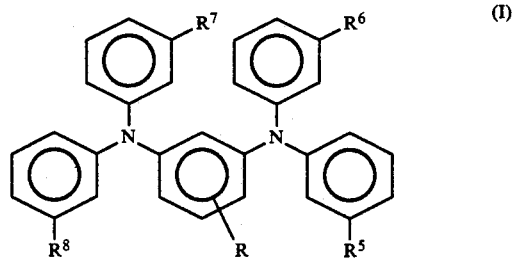

wherein $R^5$, $R^6$, $R^7$ and $R^8$ are groups substituted at meta-positions to the nitrogen atoms and represent a hydrogen atom, an alkyl group, an alkoxyl group or a halogen atom, with the proviso that at least two of $R^5$, $R^6$, $R^7$ and $R^8$ represent an alkyl group, alkoxyl group or a halogen atom, and R represents a hydrogen atom, an alkyl group, an alkoxyl group or a halogen atom.

In the photosensitive material of the present invention, the compound of general formula [I] is incorporated as the charge transport material in a binder resin. This compound is poor in the symmetry of the molecular structure, and the intermolecular mutual action is small. This means that the mutual action with a resin is large, and therefore, the compound is hardly crystallized in a resin constituting a photosensitive layer. Accordingly, it is possible to increase the concentration of the compound in the resin, and if this compound is selected and used as the charge transport material, a charge transport material-rich photosensitive material can be formed and the sensitivity can be increased because of increase of the electron mobility in the photosensitive layer.

Namely, the above-mentioned object can be attained by an electrophotographic photosensitive material comprising an electroconductive substrate and, formed thereon, a photosensitive layer containing an m-phenylenediamine compound of general formula I.

DETAILED DESCRIPTION OF THE PREFERRED EMBODIMENTS

The m-phenylenediamine compound used in the present invention is represented by general formula [I]. As the alkyl group for $R^5$, $R^6$, $R^7$ and $R^8$, there can be mentioned lower alkyl groups having 1 to 6 carbon atoms, such as a methyl group, an ethyl group, a propyl group, an isopropyl group, a butyl group, an isobutyl group, a tert-butyl group, a pentyl group and a hexyl group. As the alkoxyl group, there can be mentioned lower alkoxyl groups having 1 to 6 carbon atoms in the alkyl portion, such as a methoxy group, an ethoxy group, a propoxy group, an isopropoxy group, a butoxy group, an isobutoxy group, a tert-butoxy group, a pentyloxy group and a hexyloxy group.

Specific examples of the m-phenylenediamine compound of general formula [I] used in the present invention are shown in Table 1.

TABLE 1

(I)

| R | $R^5$ | $R^6$ | $R^7$ | $R^8$ |
| --- | --- | --- | --- | --- |
| $OC_2H_5$ | $OC_2H_5$ | $CH_3$ | $CH_3$ | $OC_2H_5$ |
| $C_2H_5$ | $C_2H_5$ | $C_2H_5$ | $C_2H_5$ | $C_2H_5$ |
| $C_3H_7$ | $C_3H_7$ | $C_3H_7$ | $C_3H_7$ | $C_3H_7$ |
| $C(CH_3)_3$ | $C(CH_3)_3$ | $C(CH_3)_3$ | $C(CH_3)_3$ | $C(CH_3)_3$ |
| $OCH_3$ | $OCH_3$ | $OCH_3$ | $OCH_3$ | $OCH_3$ |
| $OC_2H_5$ | $OC_2H_5$ | $OC_2H_5$ | $OC_2H_5$ | $OC_2H_5$ |
| $OC_2H_5$ | H | $CH_3$ | $CH_3$ | H |
| $OC_2H_5$ | $C_2H_5$ | $CH_3$ | $CH_3$ | $C_2H_5$ |
| $OC_2H_5$ | $O(CH_3)_3$ | $CH_3$ | $CH_3$ | $C(CH_3)_3$ |
| $OC_2H_5$ | $OCH_3$ | $CH_3$ | $CH_3$ | $OCH_3$ |
| $CH_3$ | $CH_3$ | $CH_3$ | $CH_3$ | $CH_3$ |
| $C_2H_5$ | $CH_3$ | $CH_3$ | $CH_3$ | $CH_3$ |
| $C_3H_7$ | $CH_3$ | $CH_3$ | $CH_3$ | $CH_3$ |
| $C(CH_3)_3$ | $CH_3$ | $CH_3$ | $CH_3$ | $CH_3$ |
| $OCH_3$ | $CH_3$ | $CH_3$ | $CH_3$ | $CH_3$ |
| $OC_2H_5$ | $CH_3$ | $CH_3$ | $CH_3$ | $CH_3$ |
| $CH_3$ | $CH_3$ | H | H | $CH_3$ |
| $CH_3$ | $CH_3$ | $C_2H_5$ | $C_2H_5$ | $CH_3$ |
| $CH_3$ | $CH_3$ | $C_3H_7$ | $C_3H_7$ | $CH_3$ |

TABLE 1-continued (I)

| R | $R^5$ | $R^6$ | $R^7$ | $R^8$ |
| --- | --- | --- | --- | --- |
| $CH_3$ | $CH_3$ | $C(CH_3)_3$ | $C(CH_3)_3$ | $CH_3$ |
| $CH_3$ | $CH_3$ | $OCH_3$ | $OCH_3$ | $CH_3$ |
| $CH_3$ | $CH_3$ | $OC_2H_5$ | $OC_2H_5$ | $CH_3$ |
| $CH_3$ | H | $CH_3$ | $CH_3$ | H |
| $CH_3$ | $C_2H_5$ | $CH_3$ | $CH_3$ | $C_2H_5$ |
| $CH_3$ | $C_3H_7$ | $CH_3$ | $CH_3$ | $C_3H_7$ |
| $CH_3$ | $C(CH_3)_3$ | $CH_3$ | $CH_3$ | $C(CH_3)_3$ |
| $CH_3$ | $OCH_3$ | $CH_3$ | $CH_3$ | $OCH_3$ |
| $CH_3$ | $OC_2H_5$ | $CH_3$ | $CH_3$ | $OC_2H_5$ |
| $C_2H_5$ | $CH_3$ | H | H | $CH_3$ |
| $C_2H_5$ | $CH_3$ | $C_2H_5$ | $C_2H_5$ | $CH_3$ |
| $C_2H_5$ | $CH_3$ | $C_3H_7$ | $C_3H_7$ | $CH_3$ |
| $C_2H_5$ | $CH_3$ | $C(CH_3)_3$ | $C(CH_3)_3$ | $CH_3$ |
| $C_2H_5$ | $CH_3$ | $OCH_3$ | $OCH_3$ | $CH_3$ |
| $C_2H_5$ | $CH_3$ | $OC_2H_5$ | $OC_2H_5$ | $CH_3$ |
| $C_2H_5$ | H | $CH_3$ | $CH_3$ | H |
| $C_2H_5$ | $C_2H_5$ | $CH_3$ | $CH_3$ | $C_2H_5$ |
| $C_2H_5$ | $C_3H_7$ | $CH_3$ | $CH_3$ | $C_3H_7$ |
| $C_2H_5$ | $C(CH_3)_3$ | $CH_3$ | $CH_3$ | $C(CH_3)_3$ |
| $C_2H_5$ | $OCH_3$ | $CH_3$ | $CH_3$ | $OCH_3$ |
| $C_2H_5$ | $OC_2H_5$ | $CH_3$ | $CH_3$ | $OC_2H_5$ |
| $C_3H_7$ | $CH_3$ | H | H | $CH_3$ |
| $C_3H_7$ | $CH_3$ | $C_2H_5$ | $C_2H_5$ | $CH_3$ |
| $C_3H_7$ | $CH_3$ | $C_3H_7$ | $C_3H_7$ | $CH_3$ |
| $C_3H_7$ | $CH_3$ | $C(CH_3)_3$ | $C(CH_3)_3$ | $CH_3$ |
| $C_3H_7$ | $CH_3$ | $OCH_3$ | $OCH_3$ | $CH_3$ |
| $C_3H_7$ | $CH_3$ | $OC_2H_5$ | $OC_2H_5$ | $CH_3$ |
| $C_3H_7$ | H | $CH_3$ | $CH_3$ | H |
| $C_3H_7$ | $C_2H_5$ | $CH_3$ | $CH_3$ | $C_2H_5$ |
| $C_3H_7$ | $C_3H_7$ | $CH_3$ | $CH_3$ | $C_3H_7$ |
| $C_3H_7$ | $C(CH_3)_3$ | $CH_3$ | $CH_3$ | $C(CH_3)_3$ |
| $C_3H_7$ | $OCH_3$ | $CH_3$ | $CH_3$ | $OCH_3$ |
| $C_3H_7$ | $OC_2H_5$ | $CH_3$ | $CH_3$ | $OC_2H_5$ |
| $C(CH_3)_3$ | $CH_3$ | H | H | $CH_3$ |
| $C(CH_3)_3$ | $CH_3$ | $C_2H_5$ | $C_2H_5$ | $CH_3$ |
| $C(CH_3)_3$ | $CH_3$ | $C(CH_3)_3$ | $C(CH_3)_3$ | $CH_3$ |
| $C(CH_3)_3$ | $CH_3$ | $OCH_3$ | $OCH_3$ | $CH_3$ |
| $C(CH_3)_3$ | $CH_3$ | $OC_2H_5$ | $OC_2H_5$ | $CH_3$ |
| $C(CH_3)_3$ | H | $CH_3$ | $CH_3$ | H |
| $C(CH_3)_3$ | $C_2H_5$ | $CH_3$ | $CH_3$ | $C_2H_5$ |
| $C(CH_3)_3$ | $C(CH_3)_3$ | $CH_3$ | $CH_3$ | $C(CH_3)_3$ |
| $C(CH_3)_3$ | $OCH_3$ | $CH_3$ | $CH_3$ | $OCH_3$ |
| $C(CH_3)_3$ | $OC_2H_5$ | $CH_3$ | $CH_3$ | $OC_2H_5$ |
| $OCH_3$ | $CH_3$ | H | H | $CH_3$ |
| $OCH_3$ | $CH_3$ | $C_2H_5$ | $C_2H_5$ | $CH_3$ |
| $OCH_3$ | $CH_3$ | $C(CH_3)_3$ | $C(CH_3)_3$ | $CH_3$ |
| $OCH_3$ | $CH_3$ | $OCH_3$ | $OCH_3$ | $CH_3$ |
| $OCH_3$ | $CH_3$ | $OC_2H_5$ | $OC_2H_5$ | $CH_3$ |
| $OCH_3$ | H | $CH_3$ | $CH_3$ | H |
| $OCH_3$ | $C_2H_5$ | $CH_3$ | $CH_3$ | $C_2H_5$ |
| $OCH_3$ | $C(CH_3)_3$ | $CH_3$ | $CH_3$ | $C(CH_3)_3$ |
| $OCH_3$ | $OCH_3$ | $CH_3$ | $CH_3$ | $OCH_3$ |
| $OCH_3$ | $OC_2H_5$ | $CH_3$ | $CH_3$ | $OC_2H_5$ |
| $OC_2H_5$ | $CH_3$ | H | H | $CH_3$ |
| $OC_2H_5$ | $CH_3$ | $C_2H_5$ | $C_2H_5$ | $CH_3$ |
| $OC_2H_5$ | $CH_3$ | $C(CH_3)_3$ | $C(CH_3)_3$ | $CH_3$ |
| $OC_2H_5$ | $CH_3$ | $OCH_3$ | $OCH_3$ | $CH_3$ |
| $OC_2H_5$ | $CH_3$ | $OC_2H_5$ | $OC_2H_5$ | $CH_3$ |

The position of the substituent R is not particularly critical, and the position of the substituent R is, for example, the 5-position.

The meta-substituted compound of general formula [I] used in the present invention can be synthesized according to various processes. For example, the meta-substituted compound can be synthesized according to the process represented by the following reaction formula:

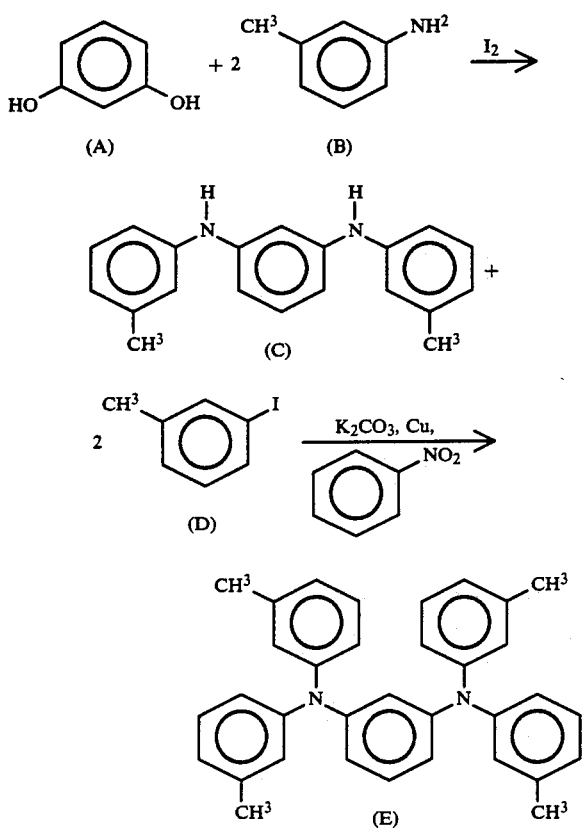

More specifically, resorcinol of formula (A) is reacted with m-toluidine of formula (B) in the presence of iodine in a nitrogen current to obtain N,N'-di(3-tolyl)-1,3-phenylenediamine of formula (C). Then, N,N'-di(3-tolyl)-1,3-phenylenediamine is reacted with iodotoluene of formula (D) in the presence of potassium carbonate and powdery copper under reflux in nitrobenzene to obtain N,N,N',N'-tetra(3-tolyl)-1,3-phenylenediamine of formula (E).

The electrophotographic photosensitive material of the present invention is characterized in that a photosensitive layer containing an m-phenylenediamine compound represented by general formula [I] is formed on an electroconductive substrate. The present invention can be applied to either a function-separated single-layer photosensitive material containing a charge generating material and a charge transport material in at least one layer formed on an electroconductive substrate, or a function-separated laminate photosensitive material comprising at least a charge generating layer and a charge transport layer, which are laminated on an electroconductive substrate. The compound of general formula [I] can be used in combination with known other charge transport material in the present invention. Known electron attractive compounds and electron donative compounds can be used as the other charge transport material. As the electron attractive compound, there can be mentioned, for example, tetracyanoethylene, 2,4,7-trinitro-9-fluorenone, 2,4,8-trinitrothioxanthone, 3,4,5,7-tetranitro-9-fluorenone, dinitrobenzene, dinitroanthrathene, dinitroacrydine, nitroanthraquinone, dinitroanthraquinone, succinic anhydride, maleic anhydride and dibromomaleic anhydride.

As the electron donative compound, there can be mentioned, for example, oxadiazole compounds such as 2,5-di(4-methylaminophenyl)-1,3,4-oxadiazole, styryl compounds such as 9-(4-diethylaminostyryl)anthrathene, carbazole compounds such as polyvinyl carbazole, pyrazoline compounds such as 1-phenyl-3-(p-dimethylaminophenyl)pyrazoline, hydrazone compounds, triphenylamine compounds, indole compounds, oxazole compounds, iso-oxazole compounds, thiazole compounds, thiadiazole compounds, imidazole compounds, pyrazole compounds, triazole compounds, and other nitrogen-containing cyclic compounds and fused polycyclic compounds. These charge transport materials can be used singly or in the form of mixtures of two or more of them. Incidentally, in the case where a film-forming charge transport material such as polyvinyl carbazole is used, use of a binder resin is not always necessary.

For example, a single-layer electrophotographic photosensitive material is prepared by forming a photosensitive layer containing a compound represented by general formula [I] as the charge transport material, a charge generating material and a binder resin on an electroconductive substrate. A laminate type electrophotographic photosensitive material is prepared by forming a charge generating layer containing a charge generating material on an electroconductive substrate by such means as vacuum deposition or coating and forming a charge transport layer containing a compound represented by general formula [I] and a binder on the charge generating layer, or vice versa by forming a similar charge transport layer on an electroconductive substrate and forming a charge generating layer containing a charge generating material on the charge transport layer by such means as vacuum deposition or coating. The charge generating layer can also be prepared by dispersing a charge generating material and a charge transport material in a binder resin and coating the dispersion.

As the charge generating material, there can be mentioned, for example, selenium, selen-tellurium, amorphous silicon, a pyrylium salt, an azo pigment, a disazo pigment, an anthanthrone pigment, a phthalocyanine pigment, an indigo pigment, a triphenylmethane pigment, a surene pigment, a toluidine pigment, a pyrazoline pigment, a perylene pigment, a quinacridone pigment and a pyrrole pigment. One or more of these charge generating materials can be used so that a desired absorption wavelength region can be obtained.

As the binder resin for the above-mentioned photosensitive layer, charge generating layer and charge transport layer, various resins can be used. For example, there can be mentioned thermoplastic resins such as a styrene polymer, a styrene/butadiene copolymer, a styrene/acrylonitrile copolymer, a styrene/maleic acid copolymer, an acrylic polymer, a styrene/acrylic copolymer, polyethylene, an ethylene/vinyl acetate copolymer, chlorinated polyethylene, polyvinyl chloride, polypropylene, a vinyl chloride/vinyl acetate copolymer, a polyester, an alkyd resin, a polyamide, a polyurethane, a polycarbonate, a polyallylate, a polysulfone, a diallyl phthalate resin, a ketone, a polyvinyl butyral resin and a polyether resin, crosslinkable thermosetting resins such as a silicone resin, an epoxy resin, a phenolic resin, a urea resin and a melamine resin, and photosetting resins such as epoxy acrylate and urethane acrylate.

These binder resins can be used singly or in the form of mixtures of two or more of them.

A solvent is used when the charge generating layer or the charge transport layer is formed by coating. For this purpose, various organic solvents can be used. For example, there can be mentioned alcohols such as methanol, ethanol, isopropanol and butanol, aliphatic hydrocarbons such as n-hexane, octane and cyclohexane, aromatic hydrocarbons such as benzene, toluene and xylene, halogenated hydrocarbons such as dichloromethane, dichloroethane, tetrachloromethane and chlorobenzene, ethers such as dimethyl ether, diethyl ether, tetrahydrofuran, ethylene glycol dimethyl ether, ethylene glycol diethyl ether and diethylene glycol dimethyl ether, ketones such as acetone, methylethylketone and cyclohexanone, esters such as ethyl acetate and methyl acetate, and dimethylformamide and dimethylsulfoxide. These solvents can be used singly or in the form of mixtures of two or more of them.

In order to increase the sensitivity of the charge generating layer, a known sensitizing agent such as terphenyl, a halonaphthoquinone or acenaphthylene can be used in combination with the above-mentioned charge generating material. Moreover, a surface active agent, a leveling agent or the like can be used in order to improve the dispersibility or coating property of the charge transport material or the charge generating material.

Various materials having an electroconductivity can be used as the electroconductive substrate. For example, there can be mentioned metals such as aluminum, copper, tin, platinum, gold, silver, vanadium, molybdenum, chromium, cadmium, titanium, nickel, palladium, indium, stainless steel and brass, plastic materials on which the above-mentioned metals are vacuum-deposited and laminated, and glass sheets coated with aluminum iodide, tin oxide, indium oxide or the like. The electroconductive substrate may be in the form of a sheet or a drum. A substrate which is electroconductive by itself or has an electroconductive surface and which shows a sufficient strength when it is actually used is preferably used in the present invention.

The laminate type electrophotographic photosensitive material is prepared by coating a charge transport layer and a charge generating layer on an electroconductive substrate in this order (photosensitive material for negative charging) or in the reverse order (photosensitive material for positive charging).

The charge transport layer is formed by dissolving or dispersing a compound of general formula [I] singly or in combination with other charge transport material in a binder resin to form a coating liquid and coating and drying the coating liquid.

The compound of the present invention as the charge transport material and the binder resin can be used at various ratios, so far as the transportation of charges is not inhibited and the crystallization is not caused. If the compound of the present invention is singly used as the charge transport material, it is preferred that the compound of general formula [I] be used in an amount of 125 to 200 parts by weight per 100 parts by weight of the binder resin.

If the amount of the compound of general formula [I] is too small and below the above-mentioned range, a sufficient sensitivity cannot be obtained. If the amount of the compound of formula [I] is too large and exceeds the above-mentioned range, the crystallization is caused or the strength of the layer is reduced.

It is preferred that the charge transport layer be formed in a thickness of 2 to 100 $\mu$m, especially about 5 to about 30 $\mu$m.

In the case where the above-mentioned charge generating material is used together with the binder resin for formation of the charge generating layer, they can be used at various ratios, but it is preferred that the binder resin be used in an amount of 1 to 300 parts by weight, especially 5 to 150 parts by weight, per 10 parts by weight of the charge generating material.

The thickness of the charge generating layer is not particularly critical, but it is preferred that the charge generating layer be formed in a thickness of 0.01 to 20 $\mu$m, especially about 0.1 to about 10 $\mu$m.

For formation of the single-layer electrophotographic photosensitive material, the charge transport material and charge generating material are used in amounts of 50 to 200 parts by weight and 3 to 10 parts by weight, respectively, per 100 parts by weight of the binder resin. In case of the single-layer electrophotographic photosensitive material, it is preferred that the compound of the present invention represented by general formula [I] be incorporated in an amount of at least 30 parts by weight per 100 parts by weight of all of the charge transport materials and in an amount of at least 25 parts by weight per 100 parts by weight of the binder resin.

In the case where the compound of the present invention represented by general formula [I] is used singly as the charge transport material, it is preferred that the compound of formula [I] be used in an amount of 70 to 200 parts by weight per 100 parts by weight of the binder resin. If the amount of the compound of general formula [I] is too small and below the above-mentioned range, a sufficient sensitivity cannot be obtained, and if the amount of the compound of formula [I] is too large and exceeds the above-mentioned range, the crystallization is caused and the strength of the photosensitive layer is reduced, resulting in degradation of the printability.

In the formation of the photosensitive material, a barrier layer can be formed on the surface of the electroconductive substrate, so far as the characteristics of the photosensitive material are not degraded. Of course, a protective layer can be formed on the surface of the photosensitive material.

When the photosensitive layer is formed by the coating means, a composition comprising the above-mentioned components at the above-mentioned ratio is formed into a coating liquid by using known means such as a roll mill, a ball mill, an attriter, a paint shaker or an ultrasonic disperser, and the coating liquid is coated and dried by known coating means. Incidentally, as pointed out hereinbefore, the charge generating layer can be formed by vacuum deposition of the above-mentioned charge generating material.

The present invention will now be described in detail with reference to the following examples that by no means limit the scope of the invention.

REFERENTIAL EXAMPLE 1

[Synthesis of N,N,N',N'-tetrakis(3-tolyl)-1,3-phenylenediamine]

In a nitrogen current, 11 g of resorcinol, 22.6 g of m-toluidine and 0.5 g of iodine were reacted under reflux for 3 days. After the reaction, the reaction mixture was cooled to room temperature, and the formed solid was washed with 500 ml of methanol to obtain N,N'-tetrakis(3-tolyl)-1,3-phenylenediamine. Then, 14.4 g of N,N'-tetrakis(3-tolyl)-1,3-phenylenediamine 20.4 g of iodobenzene, 9.7 g of potassium carbonate and 2 g of powdery copper were reacted under reflux in 100 ml of nitrobenzene for 24 hours. After the reaction, nitrobenzene and iodobenzene were removed by stream distillation, and the residue was washed with water and then with methanol. Then, the residue was added into 900 ml of benzene. The water-soluble substance was recovered by filtration and subjected to the active alumina column chromatography using benzene/hexane (1/1) as the developing solvent. The first fraction was recovered and subjected to the active alumina column chromatography using benzene/hexane (½) as the developing solvent. The first fraction was recovered and the solvent was removed by distillation. A part of the residue was dissolved in acetonitrile at room temperature, and by using the formed crystal as the seed, crystallization was carried out from acetonitrile to obtain N,N,N',N'-tetrakis(3-tolyl)-1,3-phenylenediamine (meta-substituted compound).

REFERENTIAL EXAMPLE 2

[Synthesis of N,N,N',N'-tetrakis(4-tolyl)-1,3-phenylenediamine]

N,N'-Tetrakis(4-tolyl)-1,3-phenylenediamine was synthesized in the same manner as described in Referential Example 1 except that 22.6 g of p-toluidine was used instead of m-toluidine used in Referential Example 1. Then, 14.4 g of N,N'-tetrakis(4-tolyl)-1,3-phenylenediamine, 21.8 g of iodotoluene, 9.7 g of potassium carbonate and 2 g of powdery copper were reacted under reflux in 100 ml of nitrobenzene for 24 hours. After the reaction, nitrobenzene and iodobenzene were removed by steam distillation, and the residue was washed with water and then with methanol. The residue was added into 900 ml of benzene, and the water-soluble substance was recovered by filtration and subjected to the active alumina column chromatography using benzene/hexane (1/1) as the developing solvent. The first fraction was recovered and subjected to the active alumina column chromatography using benzene/hexane (½) as the developing solvent. The first fraction was recovered and the solvent was removed by distillation, and a part of the residue was dissolved in acetonitrile at room temperature. By using the formed crystal as the seed, crystallization was carried out from acetonitrile to obtain N,N,N',N'-tetrakis(4-tolyl)-1,3-phenylenediamine (para-substituted compound).

The preparation of the electrophotographic photosensitive material will now be described.

EXAMPLE 1

A dispersion was prepared from 8 parts by weight of N,N'-di(3,5-dimethylphenyl)perylene-3,4,9,10-tetracarboxydiimide as the charge generating material, 125 parts by weight of N,N,N',N'-tetrakis(3-tolyl)-1,3-phenylenediamine (meta-substituted compound) as the charge transport material, 100 parts by weight of a polycarbonate Z resin as the binder resin and a predetermined amount of tetrahydrofuran by using an ultrasonic disperser. The dispersion was coated on an alumite-treated aluminum sheet to form a single-layer electrophotographic photosensitive material comprising a photosensitive layer having a thickness of 23 μm.

EXAMPLE 2

A single-layer electrophotographic photosensitive material was prepared in the same manner as described in Example 1 except that 150 parts by weight of N,N,N',N'-tetrakis(3-tolyl)-1,3-phenylenediamine (meta-substituted compound) was used as the charge transport material.

EXAMPLE 3

A single-layer electrophotographic photosensitive material was prepared in the same manner as described in Example 1 except that 200 parts by weight of N,N,N',N'-tetrakis(3-tolyl)-1,3-phenylenediamine (meta-substituted compound) was used as the charge transport material.

EXAMPLE 4

In 2000 parts by weight of dichloromethane were incorporated 100 parts by weight of polyvinyl butyral(-Denka Butyral #500-A supplied by Denki Kagaku Kogyo) and 100 parts by weight of the same perylene type pigment as used in Example 1, and the mixture was subjected to ultrasonic dispersing for 1 minute to prepare a coating liquid for formation of a charge generating layer. The coating liquid was coated and dried on an aluminum sheet to form a charge generating layer having a thickness of about 1 μm.

Separately, 100 parts by weight of a polycarbonate Z resin (supplied by Mitsubishi Gas Kagaku) and 125 parts by weight of the same charge transport material (meta-substituted compound) as used in Example 1 were dissolved in 900 parts by weight of tetrahydrofuran to form a coating liquid for formation of a charge transport layer. The coating liquid was coated and dried on the charge generating layer to form a charge transport layer having a thickness of about 20 μm, whereby a laminate type photosensitive material was obtained.

COMPARATIVE EXAMPLE 1

A single-layer electrophotographic photosensitive material was prepared in the same manner as described in Example 1 except that 90 parts by weight of N,N,N',N'-tetrakis(4-tolyl)-1,3-phenylenediamine (para-substituted compound) was used as the charge transport material.

COMPARATIVE EXAMPLE 2

A single-layer electrophotographic photosensitive material is prepared in the same manner as described in Example 1 except that 100 parts by weight of N,N,N',N'-tetrakis(4-tolyl)-1,3-phenylenediamine (para-substituted compound) was used as the charge transport material.

COMPARATIVE EXAMPLE 3

A single-layer electrophotographic photosensitive material was prepared in the same manner as described in Example 1 except that 90 parts by weight of N,N,N',N'-tetrakis-phenyl-1,3-phenylenediamine (unsubstituted compound) was used as the charge transport material.

COMPARATIVE EXAMPLE 4

A single-layer electrophotographic photosensitive material was used in the same manner as described in Example 1 except that 100 parts by weight of diethylaminobenzaldehyde diphenylhydrazone was used as the charge transport material.

The electrophotographic photosensitive materials prepared in the foregoing examples were evaluated in the following manner.

With respect to the charging and photosensitive characteristics, each photosensitive material was positively or negatively charged by using an electrostatic copying tester (Gentec Synthia 30M supplied by Gentec) and the surface potential Vsp (V) was measured, and by using a halogen lamp, each photosensitive material was exposed to light, the time required for reduction of the surface potential to ½ was measured and the half-value exposure quantity E½ ($\mu J/cm^2$) was calculated, while the surface potential Vrp (V) after the lapse of 0.15 second from the point of termination of the light exposure was measured. Moreover, with respect to each photosensitive material, the crystallization state was examined with the naked eye and it was checked whether or not the crystallization was caused.

The results of the measurement of the charging and photosensitive characteristics of the electrophotographic photosensitive materials obtained in the foregoing examples are shown in Table 2.

TABLE 2

| | Vo (V) | E½ ($\mu J/cm^2$) | Vrp (V) | Crystallization |
|---|---|---|---|---|
| Example 1 | 660 | 25.2 | 129 | not found |
| Example 2 | 660 | 17.0 | 112 | not found |
| Example 3 | 650 | 19.4 | 112 | not found |
| Example 4 | −660 | 23.5 | −98 | not found |
| Comparative Example 1 | — | — | — | caused |
| Comparative Example 2 | — | — | — | caused |
| Comparative Example 3 | 650 | 27.8 | 135 | not found |
| Comparative Example 4 | 640 | 33.6 | 163 | not found |

From the results shown in Table 2, it is seen that in each of the electrophotographic photosensitive materials obtained according to the present invention, charging characteristics were excellent with no crystallization, the half-value light exposure quantity was small, the sensitivity was high and the residual potential was small. In the photosensitive materials of Comparative Examples 1 and 2, the crystallization was caused. In the photosensitive material of Comparative Example 3 where the unsubstituted compound was used and photosensitive material of Comparative Example 4 where the conventional hydrazone compound was used, the sensitivity was lower and the residual potential was larger than in the photosensitive materials of the present invention.

When the unsubstituted diamine compound (Comparative Example 4) was incorporated in an increased amount as in Examples 1, 2 and 3, the crystallization was readily caused in the photosensitive layer.

From the foregoing experimental results, it was confirmed that use of the meta-substituted compound of the present invention is very effective and advantageous.

As is apparent from the foregoing description, since the meta-substituted m-phenylenediamine compound of the present invention is hardly crystallized in a resin but is sufficiently dissolved in the resin, the concentration of the compound in the resin can be increased and the mobility can be enhanced. Accordingly, an electrophotographic photosensitive material having an increased sensitivity can be obtained.

We claim:

1. An electrophotographic photosensitive material containing in a photosensitive layer an m-phenylenediamine compound represented by the following general formula [I]:

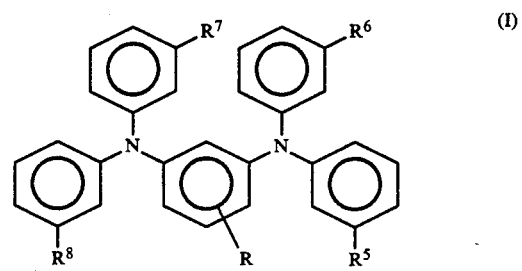

wherein $R^5$, $R^6$, $R^7$ and $R^8$ are groups substituted at meta-positions to the nitrogen atoms and represent a hydrogen atom, an alkyl group, an alkoxyl group or a halogen atom, with the proviso that at least two of $R^5$, $R^6$, $R^7$ and $R^8$ represent an alkyl group, alkoxyl group or a halogen atom, and R represents a hydrogen atom, an alkyl group, an alkoxyl group or a halogen atom.

2. An electrophotographic photosensitive material as set forth in claim 1, wherein the photosensitive layer is formed by incorporating a charge generating material and a charge transport material in a binder resin, and the m-phenylenediamine compound represented by general formula [I] is used as the charge transport material.

3. An electrophotographic photosensitive material as set forth in claim 2, wherein the m-phenylenediamine compound is incorporated in an amount of 25 to 200 parts by weight per 100 parts by weight of the binder resin.

4. An electrophotographic photosensitive material as set forth in claim 2, wherein the charge generating material is incorporated in an amount of 3 to 10 parts by weight per 100 parts by weight of the binder resin.

5. An electrophotographic photosensitive material as set forth in claim 1 wherein the m-phenylenediamine compound of formula (I) is one of the compounds set forth in Table 1 in the specification.

6. An electrophotographic photosensitive material according to claim 1 wherein said photosensitive layer comprises the m-phenylenediamine compound of formula (I) in a binder resin wherein the amount of the compound of formula (I) is from 125 to 200 parts by weight per 100 parts by weight of the binder resin.

7. An electrophotographic photosensitive material as set forth in claim 1 wherein the m-phenylenediamine compound is N,N,N′,N′-tetrakis(3-tolyl)-1,3-phenylenediamine.

* * * * *